United States Patent
Ueno et al.

[11] Patent Number: 6,057,480
[45] Date of Patent: May 2, 2000

[54] PROCESS FOR PREPARING FLUOROARYL MAGNESIUM DERIVATIVE AND PROCESS FOR PREPARING (FLUOROARYL) BORANE COMPOUND

[75] Inventors: Tsunemasa Ueno, Ikeda; Ikuyo Katsumi, Osaka; Naoko Yamamoto, Nishinomiya; Hitoshi Mitsui, Kitakatsuragi-gun, all of Japan

[73] Assignee: Nippon Shokubai Co., Ltd., Osaka, Japan

[21] Appl. No.: 08/930,708

[22] PCT Filed: Feb. 12, 1997

[86] PCT No.: PCT/JP97/00391

§ 371 Date: Oct. 16, 1997

§ 102(e) Date: Oct. 16, 1997

[87] PCT Pub. No.: WO97/31924

PCT Pub. Date: Sep. 4, 1997

[30] Foreign Application Priority Data

Feb. 28, 1996 [JP] Japan ..................................... 8-041743
Feb. 28, 1996 [JP] Japan ..................................... 8-041755

[51] Int. Cl.$^7$ ....................................................... C07F 5/02
[52] U.S. Cl. ................................ 568/6; 568/1; 260/665 G
[58] Field of Search ........................ 568/6, 1; 260/665 G

[56] References Cited

U.S. PATENT DOCUMENTS 5,399,780  3/1995  Ikeda ............................................ 568/1
5,510,536  4/1996  Ikeda .
5,693,261  12/1997  Ikeda .

FOREIGN PATENT DOCUMENTS 6-199871   7/1994   Japan .
6-247976   9/1994   Japan .
8-253485   10/1996  Japan .

OTHER PUBLICATIONS

CA:86:5504, abs of "Use of diisopropyl ether as a medium form butylmagnesium chloride production", Ratanova, Zh Prikl Khim, 49 (*), pp. 1864–1868, 1976.

CA:67:43845 abs of "Preparation of ethyl magnesium chloride in hydrocarbon solvent", Smai, Chim Ind (Milan),49(2), pp. 142–146, 1967.

*Primary Examiner*—Gary Geist
*Assistant Examiner*—Jean F Vollano
*Attorney, Agent, or Firm*—Kubovcik & Kubovcik

[57] ABSTRACT

A fluoroaryl magnesium derivative is produced by reacting aryl fluoride, hydrocarbon halide, and magnesium with one another in an ether solvent or a mixed solvent of the ether solvent and a hydrocarbon solvent. Also, a (fluoroaryl) borane compound is produced by mixing both a solution prepared by dissolving the fluoroaryl magnesium derivative into the ether solvent and another solvent prepared by dissolving the boron halide in the ether solvent with a hydrocarbon solvent having a higher boiling point than the ether solvent, so that the fluoroaryl magnesium derivative and boron halide react with each other while the ether solvent is being distilled out.

32 Claims, No Drawings

6,057,480

PROCESS FOR PREPARING FLUOROARYL MAGNESIUM DERIVATIVE AND PROCESS FOR PREPARING (FLUOROARYL) BORANE COMPOUND

This application is the national phase of PCT/J97/00391 filed Feb. 2, 1997 now WO97/31924.

TECHNICAL FIELD

The present invention relates to a process for preparing a fluoroaryl magnesium derivative which is suitably used, for example, as a reactant (organic synthetic reagent) for introducing a fluoroaryl group into various kinds of organic compounds. The present invention also relates to a process for preparing a (fluoroaryl)borane compound, such as tris (fluoroaryl)borane and bis(fluoroaryl)boryl halide, serving, for example, as an excellent cocatalyst for a metallocene catalyst (polymeric catalyst) used in a cation complex polymerization reaction.

BACKGROUND ART

A fluoroaryl magnesium derivative, which is a Grignard reagent, is well known, for example, as an excellent reactant (organic synthetic reagent) for introducing a fluoroaryl group into various kinds of organic compounds. Also, in recent years, the fluoroaryl magnesium derivative has been receiving considerable attention as a synthetic material of a tris(fluoroaryl)borane compound serving as an excellent cocatalyst for a metallocene catalyst (polymeric catalyst).

A process for preparing a fluoroaryl magnesium derivative is disclosed, for example, in J. Org. Chem., 29, 2385 (1964). More specifically, an alkyl magnesium derivative, such as ethyl magnesium bromide (EtMgBr), is dropwise to a solution prepared by dissolving pentafluorobenzene into an ether solvent, such as tetrahydrofuran (THF). Consequently, a pentafluorophenyl magnesium derivative is obtained as the fluoroaryl magnesium derivative. Japanese Laid-open Patent Application No. 247976/1994 (Tokukaihei 6-247976) discloses another process. In this process, the pentafluorophenyl magnesium derivative is obtained by adding a solution prepared by dissolving pentafluorobenzene into an ether solvent to another solution prepared by mixing an alkyl magnesium derivative with the ether solvent.

In these processes, the pentafluorophenyl magnesium derivative is obtained through an exchange reaction, in which an alkyl group in the alkyl magnesium derivative is replaced with a pentafluorophenyl group.

However, in these processes, the alkyl magnesium derivative is produced before the above exchange reaction is carried out to obtain the pentafluorophenyl magnesium derivative. In other words, since the alkyl magnesium derivative is prepared separately before obtaining the pentafluorophenyl magnesium derivative, the reaction takes place in two steps.

To solve the above problem, the present invention has a first object to provide a process for producing the fluoroaryl magnesium derivative efficiently at a low cost in a simple manner virtually in a single step reaction.

A (fluoroaryl)borane compound, particularly, tris (pentafluorophenyl)borane, is known, for example, as an excellent cocatalyst for promoting the activity of a metallocene catalyst (polymeric catalyst) used in a cation complex polymerization reaction, and recently, the metallocene catalyst has been receiving considerable attention as a polyolefin polymerization catalyst.

An example process of obtaining the above-mentioned tris(pentafluorophenyl)borane is disclosed in Proc. Chem. Soc., 1963 (July), 212. More specifically, pentafluorobenzene lithium produced by reacting bromopentafluorobenzene and butyl lithium is reacted with boron trichloride, and as a consequence, tris(pentafluorophenyl)borane is obtained. However, in this process, the reaction system must be cooled to 78° C., which makes this process almost inapplicable for industrial use.

To solve the above problem, a process using the Grignard reaction is disclosed in Z. Naturforsch., 20b, 5 (1965) as another example process of obtaining the tris (pentafluorophenyl)borane. According to this process, for example, pentafluorophenyl magnesium bromide and boron trifluoride diethyl etherate are reacted with each other in a chain ether solvent. Thus, it is not necessary to cool the reaction system to −78° C., which makes this process advantageous over the above-mentioned reaction. Further, Japanese Laid-open Patent Application No. 199871/1994 (Tokukaihei 6-199871) discloses a process of obtaining triarylborane by reacting an aryl magnesium halide derivative and boron halide in a chain ether solvent or a mixed solvent of the chain ether solvent and an aromatic hydrocarbon solvent.

However, since the above conventional processes use the chain ether solvent having a relatively low boiling point, such as diethyl ether, the reaction system must be cooled. Thus, to produce the (fluoroaryl)borane compound for industrial use, a cooling apparatus or the like is indispensable. Moreover, diethyl ether is highly inflammable. In addition, in the above conventional processes, it is difficult to control the reaction and a by-product, such as a quaternary compound of boron such as a tetrakis(fluoroaryl)borate derivative, is produced. This makes it difficult to selectively obtain the (fluoroaryl)borane compound, such as tris (fluoroaryl)borane and bis(fluoroaryl)boryl halide. Furthermore, the chain ether solvent is expensive compared with a cyclic ether solvent.

Thus, the above conventional processes have a problem that they are not readily applied for industrial use. In other words, not only are the solvents difficult to handle, but also the (fluoroaryl)borane compound, such as tris(fluoroaryl) borane and bis(fluoroaryl)boryl halide, can not be produced selectively at a low cost in a simple manner. Using a cyclic ether solvent in the above conventional processes can trigger a side-reaction, such as a ring-opening polymerization of the cyclic ether solvent. In addition, using an aromatic hydrocarbon solvent alone in the above conventional processes can reduce the yield of the (fluoroaryl)borane compound, such as tris(fluoroaryl)borane and bis(fluoroaryl)boryl halide.

Therefore, to solve the above problem, the present invention has a second object to provide a process of producing a (fluoroaryl)borane compound, such as tris(fluoroaryl) borane and bis(fluoroaryl)boryl halide, selectively at a low cost in a simple manner.

DISCLOSURE OF THE INVENTION

To fulfil the first object, the inventors of the present invention conducted research diligently on a process for preparing a fluoroaryl magnesium derivative, and discovered that a fluoroaryl magnesium derivative can be produced efficiently at a low cost in a simple manner virtually in a single step reaction by reacting aryl fluoride, hydrocarbon halide and magnesium with one another in an ether solvent or a mixed solvent of the ether solvent and a hydrocarbon solvent.

More specifically, to solve the above problem, a process for preparing a fluoroaryl magnesium derivative of the present invention is a producing process of a fluoroaryl magnesium derivative expressed by General Formula (3):

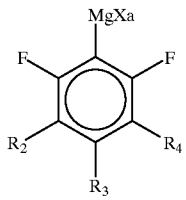

(3)

where each of $R_2$, $R_3$, and $R_4$ independently represents a hydrogen atom, a fluorine atom, a hydrocarbon group or an alkoxy group, and Xa represents a chlorine atom, a bromine atom, or an iodine atom, and the process is characterized by reacting:

(a) aryl fluoride expressed by General Formula (1):

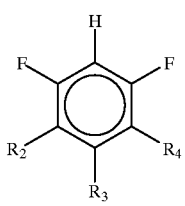

(1)

where each of $R_2$, $R_3$, and $R_4$ independently represents a hydrogen atom, a fluorine atom, a hydrocarbon group or an alkoxy group;

(b) hydrocarbon halide expressed by General Formula (2):

$$R_0 Xa \qquad (2)$$

where $R_0$ represents a hydrocarbon group, and Xa represents a chlorine atom, a bromine atom, or an iodine atom; and (c) magnesium with one another in an ether solvent or a mixed solvent of the ether solvent and a hydrocarbon solvent.

According to the above process, the reaction takes place virtually in a single step, which makes it possible to produce the fluoroaryl magnesium derivative efficiently at a low cost in a simple manner.

Also, to fulfill the second object, the inventors of the present invention conducted diligent research on a process for preparing a (fluoroaryl)borane compound, and discovered that the (fluoroaryl)borane compound, such as tris (fluoroaryl)borane and bis(fluoroaryl)boryl halide, can be produced selectively at a low cost in a simple manner by mixing a solution prepared by dissolving a fluoroaryl magnesium derivative into an ether solvent and another solution prepared by dissolving boron halide into the ether solvent with a hydrocarbon solvent having a higher boiling point than the ether solvent, so that the fluoroaryl magnesium derivative and boron halide react with each other while the ether solvent is being distilled out. The inventors further discovered that the (fluoroaryl)borane compound can be obtained from aryl fluoride virtually in a single step (so-called 1 pot) reaction by reacting the fluoroaryl magnesium derivative obtained by the above producing process with boron halide in situ, thereby making it possible to produce the (fluoroaryl)borane compound at a lower cost in a simpler manner.

In other words, to solve the above problems, a process for preparing a (fluoroaryl)borane compound of the present invention is a process for preparing a (fluoroaryl)borane compound expressed by General Formula (6):

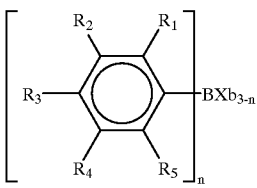

(6)

where each of $R_1$, $R_2$, $R_3$, $R_4$, and $R_5$ independently represents a hydrogen atom, a fluorine atom, a hydrocarbon group or an alkoxy group while at least one of $R_1$–$R_5$ representing a fluorine atom, Xb represents a fluorine atom, a chlorine atom, a bromine atom, or an iodine atom, and n represents 2 or 3, and the process is characterized by mixing a solution prepared by dissolving a fluoroaryl magnesium derivative expressed by General Formula (4) below into an ether solvent:

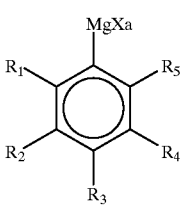

(4)

where each of $R_1$, $R_2$, $R_3$, $R_4$, and $R_5$ independently represents a hydrogen atom, a fluorine atom, a hydrocarbon group, or an alkoxy group while at least one of $R_1$–$R_5$ represents a fluorine atom, and Xa represents a chlorine atom, a bromine atom, or an iodine atom, and another solution prepared by dissolving boron halide expressed by General Formula (5) below into the ether solvent:

$$BXb_3 \qquad (5)$$

where Xb represents a fluorine atom, a chlorine atom, a bromine atom, or an iodine atom, with a hydrocarbon solvent having a higher boiling point than the ether solvent, so that the fluoroaryl magnesium derivative and boron halide react with each other while the ether solvent is being distilled out.

Also, to solve the above problems, a process for preparing a (fluoroaryl)borane compound of the present invention is a process for preparing the (fluoroaryl)borane compound expressed by General Formula (6) above, and characterized by mixing a solution prepared by dissolving the fluoroaryl magnesium derivative expressed by General Formula (4) above into an ether solvent and another solution prepared by dissolving the boron halide expressed by General Formula (5) above into the ether solvent with each other at 80° C. or below, and subsequently mixing the resulting mixed solution with a hydrocarbon solvent having a higher boiling point than the ether solvent, so that the fluoroaryl magnesium derivative and boron halide react with each other while the ether solvent is being distilled out.

According to the above process, since the reaction can be controlled easily, the ether solvent is not limited to a chain ether solvent. In other words, a cyclic ether solvent, which is relatively easy to handle, can be used as well. Also, since the resulting (fluoroaryl)borane compound, such as tris (fluoroaryl)borane and bis (fluoroaryl)boryl halide, does not produce a complex nor a quaternary compound, the (fluoroaryl)borane compound can be readily purified. Consequently, it has become possible to produce the (fluoroaryl)borane compound, such as tris(fluoroaryl)borane and bis(fluoroaryl)boryl halide, selectively at a low cost in a simple manner. In other words, the process of the present invention is advantageous over the conventional processes in terms of industrial use, and makes it possible to obtain the (fluoroaryl)borane compound, such as tris(fluoroaryl)borane and bis(fluoroaryl)boryl halide, at high yield and high selectivity.

Further, to solve the above problems, a process for preparing a (fluoroaryl)borane compound of the present invention is a process for preparing a (fluoroaryl)borane compound expressed by General Formula (10):

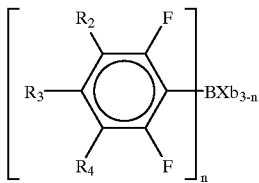

(10)

where each of $R_2$, $R_3$, and $R_4$ independently represents a hydrogen atom, a fluorine atom, a hydrocarbon group, or an alkoxy group, Xb represents a fluorine atom, a chlorine atom, a bromine atom, or an iodine atom, and n represents 2 or 3, and the process is characterized by reacting the fluoroaryl magnesium derivative expressed by General Formula (3) above and obtained by the above producing process with boron halide expressed by General Formula (5) below with each other:

$$BXb_3 \quad (5)$$

where Xb is a fluorine atom, a chlorine atom, a bromine atom, or an iodine atom.

According to the above process, in addition to the aforementioned various effects, the (fluoroaryl) borane compound can be obtained from aryl fluoride virtually in a single step (so-called 1 pot) reaction, thereby making it possible to produce the (fluoroaryl)borane compound at a lower cost in a simpler manner.

The following description will describe the present invention in detail.

To begin with, the process for preparing the fluoroaryl magnesium derivative will be explained.

The process for preparing the fluoroaryl magnesium derivative expressed by General Formula (3) above (hereinafter, referred to as fluoroaryl magnesium derivative (3)p is a process, in which aryl fluoride expressed by General Formula (1) above, the hydrocarbon halide expressed by General Formula (2) above, and magnesium are reacted with one another in an ether solvent or a mixed solvent of the ether solvent and a hydrocarbon solvent.

Aryl fluoride expressed by General Formula (1) above, which is used as a starting material of the fluoroaryl magnesium derivative (3) produced in the present invention, is a compound whose substituent groups denoted as $R_2$, $R_3$, and $R_4$ are respectively one of a hydrogen atom, a fluorine atom, a hydrocarbon group, and an alkoxy group.

The hydrocarbon group referred to herein means an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the reaction taking place in the present invention. Examples of such a functional group are: a methoxy group, a methylthio group, an N,N-dimethylamino group, an o-anise group, a p-anise group, a trimethylsilyl group, a t-butyldimethylsilyloxy group, a trifluoromethyl group, etc.

The alkoxy group is expressed by General Formula (A):

$$-OR_a \quad (A)$$

where $R_a$ represents a hydrocarbon group. Examples of the hydrocarbon group denoted as Ra in the formula are: an aryl group, a straight-chain, branched-chain, or cyclic alkyl group having up to 12 carbon atoms, and a straight-chain, branched-chain, or cyclic alkenyl group having 2–12 carbon atoms. The hydrocarbon group may further include a functional group that remains inactive to the reaction taking place in the present invention.

Examples of the alkoxy group expressed by General Formula (A) above are: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

Examples of aryl fluoride are: pentafluorobenzene, 1,2,3, 5-tetrafluorobenzene, 1,2,4,5-tetrafluorobenzene, 1,2,4-trifluorobenzene, 1,3,5-trifluorobenzene, 1,3-difluorobenzene, 2,3,5,6-tetrafluorotoluene, 2,3,4,6-tetrafluorotoluene, 2,3,5-trifluorotoluene, 2,4,6-trifluorotoluene, 2,4-difluorotoluene, 2,3,5,6-tetrafluoroanisole, 2,3,4,6-tetrafluoroanisole, 2,4,5-trifluoroanisole, 2,4,6-trifluoroanisole, 2,4-difluoroanisole, 3,5-difluoroanisole, etc.

The hydrocarbon halide expressed by General Formula (2) above is a compound in which Xa represents a chlorine atom, a bromine atom, or an iodine atom, and a substituent group denoted as $R_0$ is a hydrocarbon group. Examples of the hydrocarbon group are: an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the reaction taking place in the present invention. Examples of such a functional group are: a methoxy group, a methylthio group, an N,N-dimethylamino group, an o-anise group, a p-anise group, a trimethylsilyl group, a t-butyldimethylsilyloxy group, a trifluoromethyl group, etc.

Examples of the above hydrocarbon halide are: methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, sec-butyl chloride, sec-butyl bromide, sec-butyl iodide, t-butyl chloride, t-butyl bromide, t-butyl iodide, hexyl chloride, hexyl bromide, hexyl iodide, cyclohexyl chloride, cyclohexyl bromide, cyclohexyl iodide, allyl chloride, allyl bromide, allyl iodide, chlorobenzene, bromobenzene, iodobenzene, etc. Of all these example hydrocarbon halides, the most preferred are ethyl chloride, ethyl bromide, ethyl iodide, isopropyl chloride, isopropyl bromide, isopropyl iodide, allyl chloride, allyl bromide, and allyl iodide. One member or a mixture of two or more members selected from these examples can be used effectively.

A ratio of the hydrocarbon halide to aryl fluoride is not especially limited. However, the ratio is preferably 0.5 or above in equivalent. The ratio is more preferably in a range between 0.5 and 3.0 in equivalent, and most preferably in a range 0.8 and 1.5 in equivalent. When the ratio of the hydrocarbon halide is less than 0.5 in equivalent, there remains too much unreacted aryl fluoride to produce the fluoroaryl magnesium derivative (3) efficiently.

Magnesium in a shape with a larger surface area, such as, powders, grains, and thin pieces (ribbon), is preferable to further promote the reaction. A ratio of magnesium to aryl fluoride is not especially limited. However, the ratio is preferably 0.5 or above in equivalent. The ratio is more preferably in a range between 0.5 and 3.0 in equivalent, and most preferably in a range between 0.8 and 1.5 in equivalent. When the ratio of magnesium is less than 0.5 in equivalent, there remains too much unreacted aryl fluoride to produce the fluoroaryl magnesium derivative (3) efficiently.

The ether solvent is not especially limited as long as it is a liquid compound that remains inactive to the reaction taking place in the present invention, and into which aryl fluoride, the hydrocarbon halide, and fluoroaryl magnesium derivative (3) as a target compound can dissolve. Examples of the ether solvent are:

chain ethers, such as diethyl ether, dipropyl ether, diisopropyl ether, dibutyl ether, diisobutyl ether, dipentyl ether, diisopentyl ether, 1,2-dimethoxy ethane, 1,2-diethoxy ethane, and di(2-methoxyethyl) ether; and cyclic ethers, such as tetrahydrofuran, tetrahydropyran, and 1,4-dioxane; etc.

One member or a mixture of two or more members selected from these example compounds can be used effectively. Of all these example compounds, diethyl ether and tetrahydrofuran are preferable, because the reaction is promoted further. When a mixture of two or more members selected from these example compounds is used, it is preferable that the ether solvent includes at least diethyl ether or tetrahydrofuran.

An amount of the ether solvent is not especially limited. However, an amount in which a concentration of the resulting fluoroaryl magnesium derivative (3) is in a range between 0.1 and 80 percent by weight is preferable.

The above hydrocarbon solvent is not especially limited as long as it is a liquid compound that remains inactive to the reaction taking place in the present invention. Examples of the hydrocarbon solvent are:

straight-chain, branched-chain, or cyclic aliphatic hydrocarbons, such as pentane, isopentane, hexane, cyclohexane, heptane, octane, nonane, decane, undecane, dodecane, tridecane, tetradecane, pentadecane, hexadecane, octadecane, paraffin, and petroleum ether; and aromatic hydrocarbons, such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, and butylbenzene; etc.

One member or a mixture of two or more members selected from these example compounds can be used effectively.

A mixing ratio of the ether solvent and hydrocarbon solvent is not especially limited as long as both solvents are made into a homogeneously mixed solvent. However, a preferable ratio is in a range between 1:0 and 1:10 in volume. An amount of the mixed solvent is not especially limited, either. However, an amount in which a concentration of the resulting fluoroaryl magnesium derivative (3) is in a range between 0.1 and 80 percent by weight is preferable.

An order of aryl fluoride, the hydrocarbon halide, and magnesium when they are mixed with the ether solvent or the mixed solvent of the ether solvent and hydrocarbon solvent (hereinafter, referred to simply as solvent when referring to both kinds of solvents collectively) is not especially limited. Examples of the mixing order are:

① aryl fluoride, the hydrocarbon halide, and magnesium are mixed with the solvent substantially at the same time;

② aryl fluoride and magnesium are mixed with the solvent followed by the hydrocarbon halide;

③ aryl fluoride is mixed with the solvent first, and then the hydrocarbon halide and magnesium are mixed with the solvent substantially at the same time;

④ magnesium is mixed with the solvent first, and then aryl fluoride and the hydrocarbon halide are mixed with the solvent substantially at the same time;

⑤ magnesium, aryl fluoride, and the hydrocarbon halide are mixed with the solvent sequentially in this order; and ⑥ aryl fluoride and the hydrocarbon halide are mixed with the solvent followed by magnesium.

Of all these example orders, the most preferred is to mix aryl fluoride and magnesium with the solvent followed by the hydrocarbon halide. According to this mixing order, the fluoroaryl magnesium derivative (3) can be produced more efficiently in a simpler manner.

A mixing method of aryl fluoride and/or the hydrocarbon halide with the solvent is not especially limited. However, it is preferable to drop aryl fluoride and/or the hydrocarbon halide into the solvent continuously or sequentially, because by so doing, the reaction can be controlled more easily. A dropping method is not especially limited, and aryl fluoride or the hydrocarbon halide can be dropped to the solvent directly, or diluted with a solvent before being dropped.

A mixing temperature at which aryl fluoride and/or the hydrocarbon halide are mixed with the solvent is not especially limited. However, when mixing the hydrocarbon halide with the solvent, a preferable mixing temperature is in a range between −20° C. and a reflux temperature of the solvent. More preferably, the mixing temperature is adjusted to be in a range between −20° C. and 100° C., and most preferably, in a range between 20° C. and 70° C. When the hydrocarbon halide is mixed with the solvent within the above temperature range, the reaction can be controlled more easily. Consequently, it has become possible to produce the fluoroaryl magnesium derivative (3) more efficiently in a simpler manner. Adjusting the mixing temperature below −20° C. does not attain significant effects, and therefore, is disadvantageous for industrial use compared with a case where the mixing temperature is adjusted in the above temperature range. On the other hand, when the mixing temperature exceeds the reflux temperature of the solvent, it becomes difficult to control the reaction. The mixing temperature can be readily adjusted to be in a range between −20° C. and the reflux temperature of the solvent inclusive for industrial use.

Aryl fluoride, the hydrocarbon halide, and magnesium start to react with one another when mixed with the above non-aqueous solvent followed by stirring. As the reaction proceeds, magnesium gradually dissolves into the solvent. If there is water in the reaction system while the reaction is taking place, the resulting fluoroaryl magnesium derivative (3) reacts with water and starts to decompose. For this reason, it is preferable that the above reaction takes place under an inert gas atmosphere, such as a nitrogen gas. Also, it is preferable to displace the air inside the reaction system, namely, a reaction container, by an inert gas, such as a nitrogen gas. Further, it is preferable that the solvent, aryl fluoride, and the hydrocarbon halide do not contain water. A desiccating method of aryl fluoride, the hydrocarbon halide, and solvent is not especially limited.

A reaction temperature is preferably adjusted to be in a range between 30° C. and a reflux temperature of the solvent. More preferably, the reaction temperature is adjusted to be in a range between 30° C. and 200° C., and most preferably, in a range between 30° C. and 70° C. Consequently, it has become possible to produce the fluoroaryl magnesium derivative (3) more efficiently in a simpler manner. Adjusting the reaction temperature below 30° C. is not preferable, because the reaction becomes too slow to produce the fluoroaryl magnesium derivative (3) efficiently. On the other hand, when the reaction temperature exceeds the reflux temperature of the solvent, it becomes difficult to control the reaction.

A reaction time can be set arbitrarily to complete the reaction depending on the reaction temperature, a combination of aryl fluoride and the hydrocarbon halide, a used amount, etc. A reaction pressure is not especially limited either, and the reaction can take place under a normal (ambient), reduced, or increased pressure.

The fluoroaryl magnesium derivative (3), namely, a solution of the fluoroaryl magnesium derivative (3), is produced by the above process. In addition, hydrocarbon expressed by General Formula (B) below is produced as a by-product:

$R_0H$ (B)

where $R_0$ represents a hydrocarbon group. The solution is supplied in situ in the reaction step for producing the (fluoroaryl)borane compound when occasion demands. The hydrocarbon can be separated from the fluoroaryl magnesium derivative (3) when occasion demands, a method of which is not especially limited.

According to the above process, the reaction can take place virtually in a single step, and the fluoroaryl magnesium derivative (3) can be obtained at high yield and high selectivity. Consequently, it has become possible to produce the fluoroaryl magnesium derivative (3) efficiently at a low cost in a simple manner. The fluoroaryl magnesium derivative (3) is useful, for example, as a reactant (organic synthetic reagent) for introducing a fluoroaryl group into various kinds of organic compounds, or a synthetic material for a tris(fluoroaryl)borane compound which is an excellent cocatalyst for a metallocene catalyst (polymeric catalyst). Further, when pentafluorobenzene is used as the aryl fluoride, a pentafluorophenyl magnesium derivative (3) can be produced efficiently at a low cost in a simple manner. It is preferable to handle the resulting fluoroaryl magnesium derivative (3) in an inert gas atmosphere, such as a nitrogen gas, to prevent a reaction with water.

Next, a process for preparing the (fluoroaryl)borane compound will be explained.

The process for preparing the (fluoroaryl)borane compound of the present invention expressed by General Formula (6) above is a reaction process, in which both a solution prepared by dissolving the fluoroaryl magnesium derivative expressed by General Formula (4) above (hereinafter, referred to as fluoroaryl magnesium derivative (4)) into an ether solvent and another solution prepared by dissolving the boron halide expressed by General Formula (5) above into the ether solvent are mixed with a hydrocarbon solvent having a higher boiling point than the ether solvent, so that the fluoroaryl magnesium derivative (4) and the boron halide react with each other while the ether solvent is being distilled out.

Also, a process for preparing the (fluoroaryl)borane compound of the present invention expressed by General Formula (6) above is a reaction process, in which a solution prepared by dissolving the fluoroaryl magnesium derivative (4) into an ether solvent, and another solution prepared by dissolving the boron halide expressed by General Formula (5) above into the ether solvent are mixed with each other at 80° C. or below, and the resulting mixed solution is mixed with a hydrocarbon solvent having a higher boiling point than the ether solvent, so that the fluoroaryl magnesium derivative (4) and the boron halide react with each other while the ether solvent is being distilled out.

Further, a producing process of the (fluoroaryl)borane compound of the present invention expressed by General Formula (10) is a reaction process, in which, subsequent to the above-explained process, the resulting fluoroaryl magnesium derivative (3) and the boron halide expressed by General Formula (5) above are reacted with each other in situ.

The fluoroaryl magnesium derivative (4) used as a starting material of the (fluoroaryl)borane compound produced in the present invention is a compound in which the substituent groups denoted as $R_1$, $R_2$, $R_3$, $R_4$, and $R_5$ respectively represent one of a hydrogen atom, a fluorine atom, a hydrocarbon group, and an alkoxy group while at least one of the substituent groups $R_1$–$R_5$ represents a fluorine atom, and Xa represents a chlorine atom, a bromine atom, or an iodine atom.

Examples of the hydrocarbon group are basically the same as the aforementioned example hydrocarbon groups. Likewise, examples of the alkoxy group are basically the same as the aforementioned example alkoxy groups.

Examples of the fluoroaryl magnesium derivative (4) are: pentafluorophenyl magnesium chloride, pentafluorophenyl magnesium bromide, pentafluorophenyl magnesium iodide, 1,2,3,5-tetrafluorophenyl magnesium bromide, 1,2,4,5-tetrafluorophenyl magnesium chloride, 1,2,4-trifluorophenyl magnesium bromide, 1,3,5-trifluorophenyl magnesium iodide, 2,3,5,6-tetrafluoro-4-methylphenyl magnesium bromide, 2,5-difluorophenyl magnesium bromide, 2,5-difluoro-3-methylphenyl magnesium chloride, 2,3,4,6-tetrafluoro-5-methylphenyl magnesium bromide, 2,4,6-trifluoro-5-methylphenyl magnesium chloride, 2,3,5,6-tetrafluoro-4-methoxyphenyl magnesium bromide, 2,3,6-trifluoro-5-methoxyphenyl magnesium chloride, 2,4,6-trifluoro-5-methoxyphenyl magnesium bromide, 2,5-difluoro-3-methoxyphenyl magnesium chloride, 2,5-difluoro-4-methoxyphenyl magnesium bromide, 2-fluorophenyl magnesium bromide, 4-fluorophenyl magnesium bromide, 2-fluoro-4-methylphenyl magnesium bromide, etc. Of all these example fluoroaryl magnesium derivatives (4), the most preferred is pentafluorophenyl magnesium bromide. One member or a mixture of two or more members selected from these examples can be used effectively.

A producing process of the fluoroaryl magnesium derivative (4) is not especially limited. For example, the fluoroaryl magnesium derivative (4) can be obtained through a reaction of magnesium and fluoroaryl halide, such as fluoroaryl chloride, fluoroaryl bromide, and fluoroaryl iodide.

The fluoroaryl magnesium derivative expressed by General Formula (4) above, in which at least two substituent groups denoted as $R_1$ and $R_5$ represent fluorine atoms, that is, the fluoroaryl magnesium derivative (3), can be obtained through the producing process explained above. In other words, the fluoroaryl magnesium derivative (3) can be obtained by reacting (i) aryl fluoride having fluorine atoms at least at two positions (ortho-positions) neighboring to a hydrogen atom, that is, aryl fluoride expressed by General Formula (1) above, (ii) the hydrocarbon halide expressed by General Formula (2) above, and (iii) magnesium with one another.

The boron halide expressed by General Formula (5) above is a compound, in which Xb represents a fluorine atom, a chlorine atom, a bromine atom, or an iodine atom, and examples of which are boron trifluoride, boron trichloride, boron tribromide, and boron triiodide. Of all these examples, the most preferred is boron trifluoride. One member or a mixture of two or more members selected from these examples can be used effectively. Alternatively, the boron halide may be an ether complex, such as a diethyl ether complex and a tetrahydrofuran complex.

The ether solvent is not especially limited as long as it is a liquid compound that remains inactive to the reaction taking place in the present invention, and into which the fluoroaryl magnesium derivative (4) and boron halide can dissolve. Examples of the ether solvent are basically the same as the aforementioned example chain ethers and cyclic ethers. One member or a mixture of two or more members selected from these example compounds can be used effectively. Of all these example compounds, the most preferred are diethyl ether and tetrahydrofuran, because the reaction is promoted further. When a mixture of two or more members selected from these example compounds is used, it is preferable that the ether solvent includes at least diethyl ether or tetrahydrofuran. In the producing process of the (fluoroaryl) borane compound of the present invention, cyclic ether can be used as the ether solvent. Further, the aforementioned hydrocarbon solvent can be used besides the ether solvent to such an extent that no adverse effect is given to the reaction taking place in the present invention.

An amount of the ether solvent is not especially limited. However, an amount in which a concentration of the fluoroaryl magnesium derivative (4) or boron halide is in a range between 0.1 and 80 percent by weight is preferable. A method of dissolving the fluoroaryl magnesium derivative (4) or boron halide into the ether solvent is not especially limited. That is to say, a method of preparing a solution by dissolving the fluoroaryl magnesium derivative (4) into the ether solvent, and a method of preparing another solution by dissolving the boron halide into the ether solvent are not especially limited.

A mole ratio of the fluoroaryl magnesium derivative (4) and boron halide (the fluoroaryl magnesium derivative (4)/ boron halide) is not especially limited. However, the ratio is preferably in a range between 1.0 and 5.0. Limiting the mole ratio further to a range between 2.5 and 5.0 inclusive, more preferably to a range between 2.7 and 4.0 inclusive, and most preferably to a range between 2.8 and 3.7 inclusive, makes it possible to selectively obtain the (fluoroaryl)borane compound whose n in General Formula (6) above is 3, that is, tris(fluoroaryl)borane. Also, limiting the mole ratio further to a range between 1.0 inclusive and 2.5 exclusive, more preferably to a range between 1.2 and 2.4 inclusive, and most preferably to a range between 1.3 and 2.3 inclusive, makes it possible to mainly produce the (fluoroaryl)borane compound whose n in General Formula (6) above is 2, that is, bis(fluoroaryl)boryl halide. When the mole ratio is less than 1.0, there remains too much unreacted boron halide. On the other hand, when the mole ratio is greater than 5.0, there remains too much unreacted fluoroaryl magnesium derivative (4). Thus, it becomes impossible to produce the (fluoroaryl)borane compound, such as tris(fluoroaryl)borane and bis(fluoroaryl)boryl halide, efficiently.

The hydrocarbon solvent is not especially limited as long as it is a liquid compound that remains inactive to the reaction taking place in the present invention and has a higher boiling point than the ether solvent, and into which the (fluoroaryl)borane compound as a target compound, such as tris(fluoroaryl)borane and bis(fluoroaryl)boryl halide, can dissolve. Examples of the hydrocarbon solvent are basically the same as the aforementioned example aliphatic hydrocarbons and aromatic hydrocarbons. One member or a mixture of two or more members selected from these example compounds can be used effectively. In addition, it is preferable that the hydrocarbon solvent has a boiling point of 60° C. or above. When the hydrocarbon solvent includes the aromatic hydrocarbon, it is preferable to use the aromatic hydrocarbon to such an extent that no adverse effect is given to the reaction taking place in the present invention. Moreover, it is preferable that neither the hydrocarbon solvent nor ether solvent forms an azeotropic composition.

Suitable combinations of the ether solvent and hydrocarbon solvent are:
diethyl ether and hexane, diethyl ether and cyclohexane, diethyl ether and heptane, diethyl ether and octane, diethyl ether and IsoparE of Exxon Corp. (a mixture of isoparaffins having approximately 10 carbon atoms), diethyl ether and decane, diethyl ether and octadecane, diethyl ether and fluid paraffin, tetrahydrofuran and heptane, tetrahydrofuran and octane, tetrahydrofuran and IsoparE, tetrahydrofuran and decane, tetrahydrofuran and octadecane, tetrahydrofuran and fluid paraffin, etc.

An amount of the hydrocarbon solvent is not especially limited. However, an amount may be adjusted in such a manner that a concentration of the (fluoroaryl)borane compound as a target compound, such as tris(fluoroaryl)borane and bis(fluoroaryl)boryl halide, is preferably in a range between 0.1 and 80 percent by weight, and more preferably in a range between 0.1 and 50 percent by weight when the fluoroaryl magnesium derivative (4) and boron halide react with each other while the ether solvent is being distilled out. Particularly, limiting the concentration to a range between 0.1 and 50 percent by weight makes it possible to obtain a purer (fluoroaryl)borane compound. A method of adjusting the concentration is not especially limited. However, preferred examples are: a method of adding the hydrocarbon solvent to the reaction system occasionally when the fluoroaryl magnesium derivative (4) and boron halide react with each other while the ether solvent is being distilled out, and a method of fractionating the hydrocarbon solvent and ether solvent using a fractionating tower provided in a reactor to return the hydrocarbon solvent to the reaction system.

An order of the solution prepared by dissolving the fluoroaryl magnesium derivative (4) into the ether solvent (hereinafter, referred to as magnesium derivative solution) and another kind of solution prepared by dissolving the boron halide into the ether solvent (hereinafter, referred to as boron halide solution) when these two kinds of solutions are mixed with the hydrocarbon solvent is not especially limited. However, preferred example orders are: the magnesium derivative solution and boron halide solution are mixed with the hydrocarbon solvent substantially at the same time, and the magnesium derivative solution and boron halide solution are mixed with each other first, and thence the resulting solution is mixed with the hydrocarbon solution.

When the fluoroaryl magnesium derivative (4) touches the boron halide too long in the presence of the ether solvent, a side reaction is triggered and the yield and selectivity of the (fluoroaryl)borane compound, such as tris(fluoroaryl)borane and bis(fluoroaryl)boryl halide, are readily reduced. Thus, when the magnesium derivative solution and boron halide solution are mixed with each other, and the resulting solution is mixed with the hydrocarbon solution, it is preferable to mix the resulting solution with the hydrocarbon solvent as swiftly as possible.

Further, a mixing temperature at which the magnesium derivative solution and boron halide solution are mixed with each other is preferably adjusted to 80° C. or below, more preferably in a range between −40° C. and 70° C., and most preferably in a range between −20° C. and 50° C. This is because the side reaction can be prevented when the magnesium derivative solution and boron halide solution are mixed with each other at 80° C. or below. When the mixing temperature exceeds 80° C., it becomes difficult to control the side reaction, thereby reducing the yield and selectivity of the (fluoroaryl)borane compound, such as tris(fluoroaryl) borane and bis(fluoroaryl)boryl halide. Adjusting the mixing temperature below −40° C. does not attain significant effects, and therefore, is disadvantageous for industrial use compared with a case where the mixing temperature is adjusted in the above temperature range.

Neither a method of mixing both the magnesium derivative solution and boron halide solution with the hydrocarbon solvent nor a method of mixing the magnesium derivative solution and boron halide with each other is especially limited. However, continuous or sequential dropping is preferable.

The reaction between the fluoroaryl magnesium derivative (4) and boron halide proceeds by mixing both the magnesium derivative solution and boron halide solution with the above non-aqueous hydrocarbon solvent with stirring while the ether solvent is being distilled out. If there is water in the reaction system during the reaction, the fluoroaryl magnesium derivative (4) reacts with water and starts to decompose. Thus, it is preferable that the above reaction takes place under an inert gas atmosphere, such as a nitrogen gas. Also, it is preferable to displace the air inside the reaction system, namely, a reaction container, by an inert gas, such as a nitrogen gas. Further, it is preferable that the ether solvent, hydrocarbon solvent, and boron halide do not contain water. A desiccating method of the ether solvent, hydrocarbon solvent, and boron halide is not especially limited.

The ether solvent is distilled out before the reaction between the fluoroaryl magnesium derivative (4) and boron halide is completed. Example timings to distil the ether solvent are, but not limited to: ① after the magnesium derivative solution and/or boron halide solution are mixed with the hydrocarbon solvent, and ② while the magnesium derivative solution and/or boron halide solution are being mixed with the hydrocarbon solvent (the mixing and distilling-out are carried out concurrently); etc. Note that, however, it is preferable to distil the ether solvent as swiftly as possible for the reason explained above. Thus, the most preferable timing to distil the ether solvent is while the magnesium derivative solution and/or boron halide solution are being mixed with the hydrocarbon solvent.

A temperature at which the ether solvent is distilled out is preferably adjusted to be in a range between 30° C. and 200° C., and more preferably in a range between 30° C. and 150° C. Consequently, an amount of residual ether solvent can be reduced. Particularly, when the temperature is adjusted to be in a range between 30° C. and 150° C., a purer (fluoroaryl) borane compound can be obtained. The ether solvent can be distilled out under a normal (ambient), reduced, or increased pressure.

The reaction temperature is preferably adjusted to be in a range between 30° C. and 200° C., and more preferably, in a range between 30° C. and 170° C., and most preferably in a range between 30° C. and 150° C. Adjusting the reaction temperature to below 30° C. is not preferable, because the reaction becomes too slow to efficiently produce the (fluoroaryl)borane compound, such as tris(fluoroaryl)borane and bis(fluoroaryl)boryl halide. On the other hand, when the reaction temperature exceeds 200° C., it becomes difficult to control the reaction.

A reaction time can be set arbitrarily to complete the reaction depending on the reaction temperature, a combination of the fluoroaryl magnesium derivative (4) and boron halide, a mole ratio, etc. A reaction pressure is not especially limited, and the reaction can take place under a normal (ambient), reduced, or increased pressure.

The (fluoroaryl)borane compound expressed by General Formula (6) above is produced by the above process. Also, magnesium halide expressed by General Formula (C) below is produced as a by-product:

MgX$a$X$b$     (C)

where Xa represents a chlorine atom, a bromine atom, or an iodine atom, and Xb represents a fluorine atom, a chlorine atom, a bromine atom, or an iodine atom. The magnesium halide can be separated from the (fluoroaryl)borane compound when occasion demands, and a method of which is not especially limited. When a mixture of two or more kinds of the fluoroaryl magnesium derivative (4) is used, a mixture of more than one kind of (fluoroaryl)borane compound is obtained.

According to the above process, since the reaction can be controlled easily, the ether solvent is not limited to chain ether solvents. In other words, a cyclic ether solvent, which is relatively easy to handle, can be used as well. Also, since the resulting (fluoroaryl)borane compound, such as tris (fluoroaryl)borane and bis(fluoroaryl)boryl halide, does not produce a complex nor a quaternary compound, the (fluoroaryl)borane compound can be readily purified. Consequently, it has become possible to produce the (fluoroaryl)borane compound, such as tris(fluoroaryl)borane and bis(fluoroaryl)boryl halide, selectively at a low cost in a simple manner. In other words, the producing process of the present invention is advantageous over the conventional processes for industrial use, and makes it possible to obtain the (fluoroaryl)borane compound, such as tris(fluoroaryl) borane and bis(fluoroaryl)boryl halide, at high yield and high selectivity. The (fluoroaryl)borane compound, in particular, tris(pentafluorophenyl)borane, is useful, for example, as a cocatalyst to further promote the activity of a metallocene catalyst (polymeric catalyst). Further, when pentafluorophenyl magnesium bromide is used as the fluoroaryl magnesium derivative (4), a (pentafluorophenyl) borane compound, such as tris(pentafluorophenyl)borane and bis(pentafluorophenyl)boryl halide, can be produced efficiently at a low cost in a simple manner.

Further, the (fluoroaryl)borane compound expressed by General Formula (10) above can be obtained by reacting the fluoroaryl magnesium derivative (3) obtained by the above process for preparing the fluoroaryl magnesium derivative with the boron halide expressed by General Formula (5) above in situ. A mole ratio of the fluoroaryl magnesium derivative (3) and boron halide is not especially limited, but the aforementioned example range is also preferable herein.

A method of mixing a solution of the fluoroaryl magnesium derivative (3) and boron halide is not especially limited. The boron halide may be added to the solution collectively at one time, or dropped to the solution continuously or sequentially. The boron halide may be mixed with the solution directly or diluted with a solvent before being mixed with the solution.

A mixing temperature at which the solution of the fluoroaryl magnesium derivative (3) and boron halide are mixed with each other or a reaction temperature is not especially limited. However, it is preferable to adjust the mixing temperature and reaction temperature to be in the aforementioned example ranges, respectively. A reaction time can be set arbitrarily to complete the reaction depending on the reaction temperature, a combination of the fluoroaryl magnesium derivative (3) and boron halide, a used amount, etc. A reaction pressure is not especially limited, and the reaction can take place under a normal (ambient), reduced, or increased pressure.

The (fluoroaryl)borane compound expressed by General Formula (10) above is produced by the above process. Also, the magnesium halide expressed by General Formula (C) above is produced as a by-product. The magnesium halide can be separated from the (fluoroaryl)borane compound when occasion demands, and a method of which is not especially limited.

According to the above process, in addition to the aforementioned various effects, the (fluoroaryl)borane compound can be produced from aryl fluoride virtually in a single step (so-called 1 pot) reaction. Consequently, it has become possible to produce the (fluoroaryl)borane compound at a lower cost in a simpler manner.

Further objects, the nature and advantages of the invention will be understood by the following description. Also, the effects of the present invention will be explained clearly in the following description.

BEST MODE TO CARRYING OUT THE INVENTION

In the following, the present invention will be explained in detail by way of examples. However, the present invention is not limited to the examples below.

EXAMPLE 1

The air inside a reaction container equipped with a thermometer, a dropping funnel, a stirrer, a nitrogen gas conduit, and a reflux condenser is displaced by a nitrogen gas in a satisfactory manner. Then, 2.187 g (0.090 mole) of magnesium, 15.131 g (0.090 mole) of pentafluorobenzene as aryl fluoride, and 15 ml of diethyl ether as the solvent (ether solvent) are placed in the reaction container. Also, a mixed solution prepared by mixing 11.624 g (0.095 mole) of isopropyl bromide as the hydrocarbon halide with 10 ml of diethyl ether is placed in the dropping funnel. Both a ratio of the isopropyl bromide to pentafluorobenzene and a ratio of magnesium to pentafluorobenzene are approximately 1.06 in equivalent.

The mixed solution is dropped to the contents in the reaction container in 0.5 hour with stirring under a nitrogen gas flow. The temperature of the contents is 25° C. at the beginning of the dropping, and has risen to 57.5° C. during the dropping (which is referred to as mixing temperature).

When the dropping ends, the reactant liquid is subject to reaction (maturing) for 3 hours at 57.5° C. (reaction temperature) with stirring under a nitrogen gas flow. Consequently, pentafluorophenyl magnesium bromide is obtained as the fluoroaryl magnesium derivative (3) in the form of a diethyl ether solution.

The reaction yield of the pentafluorophenyl magnesium bromide is found by measuring $^{19}$F-NMR. More specifically, a part of the reactant liquid is put aside when the reaction ends, and a measuring sample is prepared by mixing the same with deuterobenzene under a nitrogen gas atmosphere. Here, $^{19}$F-NMR is measured under predetermined conditions. Then, an integral of a fluorine atom at the meta-position of pentafluorobenzene, and an integral of a fluorine atom at the meta-position of pentafluorophenyl group in the pentafluorophenyl magnesium bromide are computed from the resulting $^{19}$F-NMR chart first, and thence an amount of the pentafluorophenyl magnesium bromide is computed using the above two integrals.

Consequently, the reaction yield of the pentafluorophenyl magnesium bromide thus found is 83.1 percent by mole.

EXAMPLE 2

The air inside a reaction container of the same kind as the one used in Example 1 is displaced by a nitrogen gas in a satisfactory manner. Then, 2.183 g (0.090 mole) of magnesium, 15.126 g (0.090 mole) of pentafluorobenzene, and 15 ml of tetrahydrofuran as the solvent (ether solvent) are placed in the reaction container. Also, a mixed solution prepared by mixing 11.646 g (0.095 mole) of isopropyl bromide with 10 ml of tetrahydrofuran is placed in the dropping funnel. Both a ratio of the isopropyl bromide to pentafluorobenzene and a ratio of magnesium to pentafluorobenzene are approximately 1.06 in equivalent.

Then, the mixed solution is dropped to the contents in the reaction container in 50 minutes with stirring under a nitrogen gas flow. The temperature of the contents is 25° C. at the beginning of the dropping, and has risen to 50.0° C. during the dropping (which is referred to as mixing temperature).

When the dropping ends, the reactant liquid is subject to reaction (maturing) for 3 hours at 50.0° C. (reaction temperature) with stirring under a nitrogen gas flow. Consequently, pentafluorophenyl magnesium bromide is obtained in the form of a tetrahydrofuran solution.

The reaction yield of the pentafluorophenyl magnesium bromide found in the same manner as Example 1 is 90.1 percent by mole.

EXAMPLE 3

The air inside a reaction container of the same kind as the one used in Example 1 is displaced by a nitrogen gas in a satisfactory manner. Then, 2.217 g (0.091 mole) of magnesium, 15.318 g (0.091 mole) of pentafluorobenzene, 15 ml of diethyl ether as the ether solvent, and 5 ml of toluene as the hydrocarbon solvent are placed in the reaction container. Also, a mixed solution prepared by mixing 12.364 g (0.101 mole) of isopropyl bromide with 10 ml of diethyl ether is placed in the dropping funnel. A ratio of the isopropyl bromide to pentafluorobenzene is approximately 1.11 in equivalent and a ratio of magnesium to pentafluorobenzene is approximately 1.00 in equivalent.

The mixed solution is dropped to the contents in the reaction container in 0.5 hour with stirring under a nitrogen gas flow. The temperature of the contents is 25° C. at the beginning of the dropping, and has risen to 61.0° C. during the dropping (which is referred to as mixing temperature). Here, a mixing ratio of diethyl ether and toluene is 5:1 in volume.

When the dropping ends, the reactant liquid is subject to reaction (maturing) for 3 hours at 61.0° C. (reaction temperature) with stirring under a nitrogen gas flow. Consequently, pentafluorophenyl magnesium bromide is obtained in the form of a mixed solution of diethyl ether and toluene.

The reaction yield of the pentafluorophenyl magnesium bromide found in the same manner as Example 1 is 80.0 percent by mole.

EXAMPLE 4

The manipulation, reaction, and measurement are carried out in the same manner as Example 3 except that the reaction time (maturing time) is extended to 5 hours from 3 hours, and the reaction yield of the resulting pentafluorophenyl magnesium bromide is 82.2 percent by mole.

EXAMPLE 5

Herein, a 4-neck flask of 100 ml equipped with a thermometer, a dropping funnel, a stirrer, a nitrogen gas conduit, and a Dimroth condenser is used as a mixing container. The air inside the mixing container is displaced by a nitrogen gas several times, after which 35 ml of tetrahydrofuran as the ether solvent, 1.8159 g (12.81 mmole) of a boron trifluoride tetrahydrofuran complex as the boron halide are placed in the mixing container. Also, 35 ml of a tetrahydrofuran solution (magnesium derivative solution) including 37.9 mmole of pentafluorophenyl magnesium bromide as the fluoroaryl magnesium derivative (4) is placed in the dropping funnel. Here, a mole ratio of the pentafluorophenyl magnesium bromide and boron trifluoride tetrahydrofuran complex is 3.0.

Then, the tetrahydrofuran solution is dropped to the contents (boron halide solution) in the mixing container in 15 minutes at 25° C. (mixing temperature) with stirring under a nitrogen gas flow to obtain a mixed solution. The following reaction and manipulation are carried out immediately using the resulting mixed solution.

A 4-neck flask of 300 ml equipped with a thermometer, a dropping funnel, a stirrer, a nitrogen gas conduit, and a Liebig condenser is used as a reaction container herein. A receiver is attached to the edge of the outlet of the Liebig condenser, to which a so-called evacuation line furnished with a vacuum pump or the like is connected. After the air inside the reaction container is displaced by a nitrogen gas several times, 200 ml of IsoparE of Exxon Corp. is placed in the reaction container as the hydrocarbon solvent. Also, the above mixed solution is placed in the dropping funnel. The pressure inside the reaction container, namely, the reaction system, is a normal pressure at this point.

Then, the hydrocarbon solvent is heated to 60° C. with stirring under a nitrogen gas flow, after which the mixed solution is dropped to the hydrocarbon solvent while keeping the hydrocarbon solvent at 60° C. When about half an amount of the mixed solution has been dropped, a pressure inside the reaction system is reduced gradually to start the distilling-out of tetrahydrofuran while the remaining of the mixed solution is kept being dropped. Then, the dropping of the mixed solution completes in 1.5 hour. The pressure inside the reaction system at this point is reduced to 250 mmHg.

When the dropping ends, the reactant liquid is subject to reaction (maturing) for 3 hours at 60° C. (reaction temperature) with stirring under a nitrogen gas flow while the pressure inside the reaction system is further reduced. The pressure inside the reaction system when the reaction ends is reduced to 80 mmHg.

When the reaction ends, the reactant liquid is cooled to room temperature, and filtered under a nitrogen gas atmosphere. Consequently, tris(pentafluorophenyl)borane is obtained as the (fluoroaryl)borane compound in the form of a solution of the hydrocarbon solvent.

The yield of the tris(pentafluoropheny)borane is found by measuring $^{19}$F-NMR. More specifically, $^{19}$F-NMR is measured under predetermined conditions using p-fluorotoluene as an internal standard. Then, an integral of a fluorine atom of p-fluorotoluene, and an integral of a fluorine atom at the ortho-position of pentafluorophenyl group in the tris (pentafluorophenyl)borane are computed from the resulting $^{19}$F-NMR chart first, and thence an amount of the tris (pentafluorophenyl)borane is computed using the above two integrals. Consequently, the yield of the tris (pentafluorophenyl)borane thus found is 76.8 percent by mole.

EXAMPLE 6

The air inside a mixing container of the same kind as the one used in Example 5 is displaced with a nitrogen gas several times, after which 35 ml of tetrahydrofuran and 1.7712 g (12.49 mmole) of a boron trifluoride tetrahydrofuran complex are placed in the mixing container. Also, 35 ml of a tetrahydrofuran solution containing 37.81 mmole of pentafluoropheyl magnesium bromide is placed in the dropping funnel. A mole ratio of the pentafluorophenyl magnesium bromide and boron trifluoride tetrahydrofuran complex is 3.0.

Then, the tetrahydrofuran solution is dropped to the content in the mixing container in 5 minutes at 25° C. (mixing temperature) with stirring under a nitrogen gas flow to obtain a mixed solution. Then, the following reaction and manipulation are carried out immediately using the mixed solution thus obtained.

The air inside a reaction container of the same kind as the one used in Example 5 is displaced with a nitrogen gas several times, after which 200 ml of IsoparE of Exxon Corp. is placed in the reaction container as the hydrocarbon solvent. Also, the above mixed solution is placed in the dropping funnel. The pressure inside the reaction container, namely, the reaction system, is a normal pressure at this point.

Then, the hydrocarbon solvent is heated to 85° C. with stirring under a nitrogen gas flow, after which the mixed solution is dropped to the hydrocarbon solvent while the hydrocarbon solvent is kept at 85° C. When about half an amount of the mixed solution has been dropped, the pressure inside the reaction system is reduced gradually to start the distilling-out of tetrahydrofuran while the remaining of the mixed solution is kept being dropped. Then, the dropping of the mixed solution completes in 1.5 hour. The pressure inside the reaction system at this point is reduced to 450 mmHg.

When the dropping ends, the reactant liquid is subject to reaction (maturing) for 1 hour at 60° C. (reaction temperature) with stirring under a nitrogen gas flow while the pressure inside the reaction system is further reduced. The pressure inside the reaction system when the reaction ends is reduced to 80 mmHg.

When the reaction ends, the reactant liquid is cooled to room temperature, and filtered under a nitrogen gas atmosphere. Consequently, tris(pentafluorophenyl)borane is obtained as the (fluoroaryl)borane compound in the form of a solution of the hydrocarbon solvent.

The yield of tris(pentafluoropheny)borane found in the same manner as Example 5 is 69.2 percent by mole. Further, an extract is obtained from the solids (insoluble substance) obtained by the filtration using diethyl ether, and an amount of the tris(pentafluorophenyl)borane contained in the extract is found in the same manner as Example 5. Then, it turns out the extract contains the tris(pentafluorophenyl)borane in an amount corresponding to 22.5 percent by mole in yield. Thus, the overall yield of the tris(pentafluorophenyl)borane is 91.7 percent by mole herein.

EXAMPLE 7

The air inside a mixing container of the same kind as the one used in Example 5 is displaced with a nitrogen gas several times. Then, 10 ml of diethyl ether as the ether solvent and 3.395 g (23.90 mmole) of a boron trifluoride diethyl etherate as the boron halide are placed in the mixing container. Also, 35 ml of a diethyl ether solution containing 38.57 mmole of pentafluorophenyl magnesium bromide is placed in the dropping funnel. A mole ratio of the pentafluorophenyl magnesium bromide and boron trifluoride diethyl etherate is 1.6.

Then, the diethyl ether solution is dropped to the contents in the mixing container in 30 minutes at 25° C. (mixing temperature) with stirring under a nitrogen gas flow to obtain a mixed solution. Then, the following reaction and manipulation are carried out immediately using the mixed solution thus obtained.

Here, a 4-neck flask of 300 ml equipped with a thermometer, a dropping funnel, a stirrer, a nitrogen conduit, and a Liebig condenser is used as a reaction container. A receiver is attached to the edge of the outlet of the Liebig condenser. After the air inside the reaction container is displaced by a nitrogen gas for several times, 200 ml of IsoparE is placed in the reaction container as the hydrocarbon solvent. Also, the above mixed solution is placed in the dropping funnel. The pressure inside the reaction container, namely, reaction system, is a normal pressure at this point.

Then, the hydrocarbon solvent is heated to 90° C. with stirring under a nitrogen gas flow, after which the mixed solution is dropped to the hydrocarbon solvent in 1 hour while the hydrocarbon solvent is kept at 90° C. The distilling-out of the distillate containing diethyl ether is started concurrently with the dropping of the mixed solution.

When the dropping ends, the reactant liquid is heated to 110° C. (reaction temperature) under a nitrogen flow and subject to reaction (maturing) for 1 hour with stirring under a nitrogen gas flow while being kept at 110° C.

When the reaction ends, the reactant liquid is cooled to room temperature, and filtered under a nitrogen gas atmosphere. Consequently bis(pentafluorophenyl)boryl fluoride is obtained as the (fluoroaryl)borane compound in the form of a solution (filtrate) of the hydrocarbon solvent.

The yield of the bis(pentafluoropheny)boryl fluoride found in the same manner as Example 5 is 92.5 percent by mole.

EXAMPLE 8

Here, a 4-neck flask of 300 ml equipped with a thermometer, two dropping funnels, a stirrer, a nitrogen gas conduit, and a Liebig condenser is used as a reaction container. A receiver is attached to the edge of the outlet of the Liebig condenser, to which a so-called evacuation line furnished with a vacuum pump or the like is connected. After the air inside the reaction container is displaced by a nitrogen gas for several times, 200 ml of IsoparE of Exxon Corp. is placed in the reaction container as the hydrocarbon solvent. On the other hand, 35 ml of tetrahydrofuran and 1.8128 g (12.79 mmole) of a boron trifluoride tetrahydrofuran complex are placed in one of the two dropping funnels, while 35 ml of a tetrahydrofuran solution containing 37.30 mmole of pentafluorophenyl magnesium bromide is placed in the other dropping funnel. A mole ratio of the pentafluorophenyl magnesium bromide and the boron trifluoride tetrahydrofuran complex is 2.9. The pressure inside the reaction container, namely, the reaction system, is a normal pressure at this point.

Then, the hydrocarbon solvent is heated to 64° C. with stirring under a nitrogen gas flow, after which the tetrahydrofuran solution is dropped to the hydrocarbon solvent from both the dropping funnels substantially at the same time while keeping the hydrocarbon solvent at 64° C. When about half an amount of the tetrahydrofuran solution in each dropping funnel has been dropped, the pressure inside the reaction system is reduced gradually to start the distilling-out of tetrahydrofuran while the remaining of the mixed solution is kept being dropped from both the dropping funnels. Then, the dropping of the mixed solution completes in 1 hour. The pressure inside the reaction system is reduced to 250 mmHg, and the temperature of the reactant liquid has dropped to 55° C. at this point.

When the dropping ends, the reactant liquid is subject to reaction (maturing) for 2 hours at 55° C. (reaction temperature) with stirring under a nitrogen gas flow while the pressure inside the reaction system is further reduced. The pressure inside the reaction system when the reaction ends is reduced to 80 mmHg.

When the reaction ends, the reactant liquid is cooled to room temperature, and filtered under a nitrogen gas atmosphere. Consequently, tris(pentafluorophenyl)borane is obtained as the (fluoroaryl)borane compound in the form of a solution of the hydrocarbon solvent.

The yield of the tris(pentafluoropheny)borane found in the same manner as Example 5 is 41.9 percent by mole. Further, an extract is obtained from the solids (insoluble substance) obtained by the filtration using diethyl ether, and an amount of the tris (pentafluorophenyl) borane contained in the extract is found in the same manner as Example 5. Then, it turns out that the extract contains the tris(pentafluorophenyl)borane in an amount corresponding to 21.4 percent by mole in yield. Thus, the overall yield of the tris (pentafluorophenyl)borane is 63.3 percent by mole herein.

EXAMPLE 9

The (fluoroaryl)borane compound is produced using aryl fluoride as a starting material. More specifically, the inside of a reaction container equipped with a thermometer, a dropping funnel, a stirrer, a nitrogen gas conduit, and a reflux condenser is displaced by a nitrogen gas in a satisfactory manner. Then, 2.320 g (0.095 mole) of magnesium, 15.110 g (0.090 mole) of pentafluorobenzene as aryl fluoride, and 20 ml of diethyl ether as the solvent (ether solvent) are placed in the reaction container. Also, a mixed solution prepared by mixing 11.707 g (0.095 mole) of isopropyl bromide as the hydrocarbon halide with 5 ml of diethyl ether is placed in the dropping funnel. Both a ratio of the isopropyl bromide to pentafluorobenzene and a ratio of magnesium to pentafluorobenzene are approximately 1.06 in equivalent.

The mixed solution is dropped to the contents in the reaction container in 1 hour with stirring under a nitrogen gas flow. When the dropping ends, the reactant liquid is subject to reaction (maturing) for 3 hours at 65.0° C. (reaction temperature) with stirring under a nitrogen gas flow. After the reaction ends, the reactant liquid is diluted with 20 ml of diethyl ether. Consequently, pentafluorophenyl magnesium bromide is obtained as the fluoroaryl magnesium derivative (3) in the form of a solution of diethyl ether.

The reaction yield of the pentafluorophenyl magnesium bromide found in the same manner as Example 1 above is 88.0 percent by mole. Further, the following reaction is carried out using the resulting pentafluorophenyl magnesium bromide in the form of the solution of diethyl ether.

The air inside a reaction container equipped with a thermometer, a dropping funnel, a stirrer, a nitrogen gas conduit, and a reflux condenser is displaced by a nitrogen gas in a satisfactory manner. Then, 3.198 g of a boron trifluoride diethyl etherate and 20 ml of diethyl ether are placed in the reaction container. Also, the pentafluorophenyl magnesium bromide in the form of the diethyl ether solution is placed in the dropping funnel. A mole ratio of the pentafluorophenyl magnesium bromide and boron trifluoride diethyl etherate is 3.5.

Then, the diethyl ether solution in the dropping funnel is dropped to the contents in the reaction container in 0.5 hour with stirring under a nitrogen gas flow. The temperature of the contents at the beginning of the dropping is 25° C., and has risen to 36° C. during the dropping (which is referred to as mixing temperature).

When the dropping ends, the reactant liquid is subject to reaction (maturing) for 3 hours at 37° C. (reaction temperature) with stirring under a nitrogen gas flow. Consequently, tris(pentafluorophenyl)borane as the (fluoroaryl)borane compound is obtained in the form of a diethyl ether solution.

The yield of the tris(pentafluorophenyl)borane with respect to boron trifluoride found in the same manner as Example 5 is 88.7 percent by mole.

EXAMPLE 10

The (fluoroaryl)borane compound is produced using aryl fluoride as a starting material. More specifically, the air inside a reaction container of the same kind as the one used in Example 9 is displaced by a nitrogen gas in a satisfactory manner. Then, 2.184 g (0.090 mole) of magnesium, 15.128 g (0.090 mole) of pentafluorobenzene, and 15 ml of diethyl ether are placed in the reaction container. Also, a mixed solution prepared by mixing 12.189 g (0.099 mole) of isopropyl bromide with 10 ml of diethyl ether is placed in the dropping funnel. A ratio of the isopropyl bromide to pentafluorobenzene is 1.10 in equivalent, and a ratio of magnesium to pentafluorobenzene is 1.00 in equivalent.

Then, the mixed solution is dropped to the contents in the reaction container in 55 minutes with stirring under a nitrogen gas flow. When the dropping ends, the reactant liquid is subject to reaction (maturing) for 4 hours at 61.0° C. (reaction temperature) with stirring under a nitrogen gas flow. Consequently, pentafluorophenyl magnesium bromide as the fluoroaryl magnesium derivative (3) is obtained in the form of a diethyl ether solution.

The reaction yield of the pentafluorophenyl magnesium bromide found in the same manner as Example 1 is 85.7 percent by mole. Subsequently, the following reaction is carried out using the resulting pentafluorophenyl magnesium bromide in the form of the diethyl ether solution.

The air inside a mixing container equipped with a thermometer, a dropping funnel, a stirrer, a nitrogen gas conduit, and a reflux condenser is displaced by a nitrogen gas in a satisfactory manner. Then, 2.994 g (0.021 mole) of a boron trifluoride diethyl etherate and 20 ml of diethyl ether are placed in the mixing container. Also, the pentafluorophenyl magnesium bromide in the form of the diethyl ether solution and 25 ml of diethyl ether are placed in the dropping funnel. A mole ratio of the pentafluorophenyl magnesium bromide and the boron trifluoride diethyl etherate is 3.66.

Then, the diethyl ether solution in the dropping funnel is dropped to the content in the mixing container in 80 minutes with stirring under a nitrogen gas flow. When the dropping ends, the resulting mixed solution is stirred overnight at room temperature under a nitrogen gas flow. Then, the following reaction and manipulation are carried out using the resulting mixed solution.

The air inside a reaction container equipped with a thermometer, a dropping funnel, a stirrer, a nitrogen gas conduit, and a reflux condenser is displaced by a nitrogen gas in a satisfactory manner, after which 300 ml of IsoparE of Exxon Corp. is placed in the reaction container as the hydrocarbon solvent. Also, the mixed solution prepared in the above manner is placed in the dropping funnel.

Then, the hydrocarbon solvent is heated to 115° C. with stirring under a nitrogen gas flow, after which the mixed solution is dropped to the hydrocarbon solvent in 1 hour while keeping the hydrocarbon solvent at 115° C. Here, the distilling out of the distillate containing diethyl ether is started concurrently with the dropping of the mixed solution. When the dropping ends, the distillate containing diethyl ether is further distilled out while the temperature inside the reaction container is gradually raised to 123° C. (reaction temperature) under a nitrogen gas flow.

When the reaction ends, the reactant liquid is cooled to room temperature, and filtered under a nitrogen gas atmosphere. Consequently, tris(pentafluorophenyl)borane is obtained as the (fluoroaryl)borane compound in the form of a solution (filtrate) of the hydrocarbon solvent.

The yield of the tris(pentafluorophenyl)borane with respect to boron trifluoride found in the same manner as Example 5 is 73.1 percent by mole.

EXAMPLE 11

Here, a 4-neck flask of 1,000 ml equipped with a thermometer, a dropping funnel, a stirrer, a nitrogen gas conduit, and a Dimroth condenser is used as a mixing container. The air inside the mixing container is displaced by a nitrogen gas several times, after which 350 ml of diethyl ether and 33.7127 g (237.53 mmole) of a boron trifluoride diethyl etherate are placed in the mixing container. Also, 360 ml of a diethyl ether solution containing 707.4 mmole of pentafluorophenyl magnesium bromide is placed in the dropping funnel. A mole ratio of the pentafluorophenyl magnesium bromide and boron trifluoride diethyl etherate is 3.0. The pressure inside the mixing container is a normal pressure at this point.

Then, the diethyl ether solution in the dropping funnel is dropped to the contents in the mixing container in 1 hour with stirring under a nitrogen gas flow. The temperature inside the mixing container at the beginning of the dropping is 25° C., and the temperature of the contents during the dropping has risen to 34° C. Consequently, 670.8 g of a mixed solution is obtained. Then, the following reaction and manipulation are carried out immediately using the resulting mixed solution.

Here, a 4-neck flask of 3,000 ml equipped with a thermometer, a dropping funnel, a stirrer, a nitrogen gas conduit, an Oldershaw fractionating tower with tens of plates is used as a reaction container. A receiver is attached to a predetermined position, so that a distillate from the fractionating tower is collected therein. After the air inside the reaction container is displaced by a nitrogen gas for several times, 1,056.0 g of IsoparE of Exxon Corp. is placed in the reaction container as the hydrocarbon solvent. Also, the above mixed solution is placed in the dropping funnel.

The pressure inside the reaction container, namely, the reaction system, is a normal pressure at this point.

Then, the hydrocarbon solvent is heated to 95° C. with stirring under a nitrogen gas flow, after which the mixed solution is dropped to the hydrocarbon solvent in 1 hour while keeping the hydrocarbon solvent at 95° C. The distilling-out of the distillate containing diethyl ether is started concurrently with the dropping of the mixed solution. When the dropping ends, the temperature inside the reaction container is raised gradually to 125° C. (reaction temperature) to further distil the distillate, while subjecting the reaction system to reaction (maturing) for a predetermined time at 125° C. Here, 404.6 g out of the entire distillate weighing 792.9 g is diethyl ether. Thus, the recovery of diethyl ether is 92.1 percent by weight. The concentration of (pentafluorophenyl)borane in the post-reaction reactant liquid found in a similar manner to Example 5 is 12.9 percent by weight.

When the reaction ends, the reactant liquid is diluted with 2,275.7 g of IsoparE. The diluted reactant liquid is cooled to room temperature, and filtered under a nitrogen gas atmosphere. Consequently, tris(pentafluorophenyl)borane is obtained as the (fluoroaryl)borane compound in the form of a solution (filtrate) of the hydrocarbon solvent.

The yield of the tris(pentafluorophenyl)borane found in the same manner as Example 5 is 95.9 percent by mole. An amount of residue diethyl ether in the solution (filtrate) is found by measuring $^1$H-NMR using p-fluorotoluene as an internal standard. Then, an amount of residue diethyl ether with respect to the tris(pentafluorophenyl)borane is 4.7 percent by mole.

The art of the present invention is described by way of Embodiment and Examples in "BEST MODE TO CARRYING OUT THE INVENTION" column, and the present invention shall not be construed restrictive. The present invention may be varied in many ways within the spirit and scope of the invention.

POSSIBLE INDUSTRIAL APPLICATION

If the producing process of a fluoroaryl magnesium derivative of the present invention is adopted, the reaction step can be composed of virtually a single step, thereby making it possible to produce the fluoroaryl magnesium derivative efficiently at a low cost in a simple manner. The fluoroaryl magnesium derivative is suitably used, for example, as a reactant (organic synthetic reagent) for introducing a fluoroaryl group into various kinds of organic compounds.

Also, if the producing process of a (fluoroaryl)borane compound of the present invention is adopted, it becomes possible to produce the (fluoroaryl)borane, such as a tris(fluoroaryl)borane compound and bis(fluoroaryl)boryl halide, selectively at a low cost in a simple manner. In other words, the producing process of the present invention is advantageous for industrial use compared with the conventional processes, and makes it possible to obtain the (fluoroaryl)borane compound, such as a tris(fluoroaryl)borane compound and bis(fluoroaryl)boryl halide, at high yield and high selectivity. The (fluoroaryl)borane compound is used, for example, as an excellent cocatalyst for a metallocene catalyst (polymeric catalyst) used in a cation complex polymerization reaction.

Further, if the above producing process of the fluoroaryl magnesium derivative and the producing process of the (fluoroaryl)borane compound are adopted, it becomes possible to produce the (fluoroaryl)borane compound from aryl fluoride virtually in a single step (so-called 1 pot) reaction. Thus, the (fluoroaryl)borane compound can be produced at a lower cost in a simpler manner.

We claim:

1. A process for preparing a fluoroaryl magnesium derivative expressed by Formula (3):

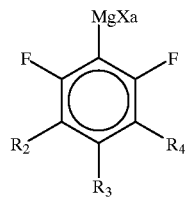

(3)

where each of $R_2$, $R_3$ and $R_4$ represents a hydrogen atom, a fluorine atom, a hydrocarbon group, or an alkoxy group, and Xa represents a chlorine atom, a bromine atom, or an iodine atom, said process comprising reacting
(a) aryl fluoride expressed by Formula (1):

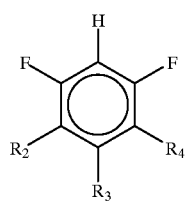

(1)

where each of $R_2$, $R_3$, and $R_4$, represents a hydrogen atom, a fluorine atom, a hydrocarbon group, or an alkoxy group, (b) hydrocarbon halide expressed by Formula (2)

$R_0 Xa$ (2)

where $R_0$, represents a hydrocarbon group, and Xa represents a chlorine atom, a bromine atom, or an iodine atom, and (c) magnesium with one another in an ether solvent or a mixed solvent of the ether solvent and a hydrocarbon solvent, the ether solvent or the mixed solvent being mixed with said aryl fluoride and magnesium followed by said hydrocarbon halide.

2. The process for preparing a fluoroaryl magnesium derivative of claim 1, wherein a mixing temperature at which the ether solvent or mixed solvent is mixed with the hydrocarbon halide is in a range between −20° C. and a reflux temperature of the ether solvent or mixed solvent, whichever is used.

3. The process for preparing a fluoroaryl magnesium derivative of claim 1, wherein a reaction temperature is in a range between 30° C. and a reflux temperature of the ether solvent or mixed solvent, whichever is used.

4. The process for preparing a fluoroaryl magnesium derivative of claim 1, wherein a mole ratio of the hydrocarbon halide to aryl fluoride is 0.5 or greater.

5. The process for preparing a fluoroaryl magnesium derivative of claim 1, wherein a mole ratio of magnesium to aryl fluoride is 0.5 or greater.

6. The process for preparing a fluoroaryl magnesium derivative of claim 1, wherein a mixing ratio of the ether solvent and the hydrocarbon solvent is in a range between 1:0 and 1:10 in volume.

7. The process for preparing a fluoroaryl magnesium derivative of claim 1, wherein an amount of the ether solvent or the mixed solvent is adjusted in such a manner that a concentration of the fluoroaryl magnesium derivative is in a range between 0.1 and 80 percent by weight.

8. The process for preparing a fluoroaryl magnesium derivative of claim 1, wherein said aryl fluoride is pentafluorobenzene.

9. The process for preparing a fluoroaryl magnesium derivative of claim 1, wherein the hydrocarbon halide is selected from the group consisting of ethyl chloride, ethyl bromide, ethyl iodide, isopropyl chloride, isopropyl bromide, isopropyl iodide, allyl chloride, allyl bromide, and allyl iodide.

10. The process for preparing a fluoroaryl magnesium derivative of claim 1, wherein the ether solvent contains diethyl ether and/or tetrahydrofuran.

11. A Process for preparing a (fluoroaryl)borane compound expressed by Formula (6):

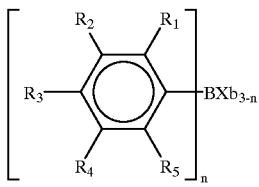

(6)

where each of $R_1$, $R_2$, $R_3$, $R_4$, and $R_5$ represents a hydrogen atom, a fluorine atom, a hydrocarbon group, or an alkoxy group, while at least one of $R_1$–$R_5$ represents a fluorine atom, Xb represents a fluorine atom, a chlorine atom, a bromine atom, or an iodine atom, and n represents 2 or 3, said process comprising mixing both a solution prepared by dissolving a fluoroaryl magnesium derivative expressed by Formula (4) below in an ether solvent:

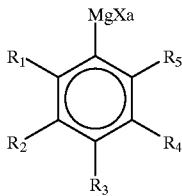

(4)

where each of $R_1$, $R_2$, $R_3$, $R_4$, and $R_5$ represents a hydrogen atom, a fluorine atom, a hydrocarbon group, or an alkoxy group, while at least one of $R_1$–$R_5$ represents a fluorine atom, and Xa represents a chlorine atom, a bromine atom, or an iodine atom, and a solution prepared by dissolving boron halide expressed by Formula (5) below in the ether solvent:

$$BXb_3 \qquad (5)$$

where Xb represents a fluorine atom, a chlorine atom, a bromine atom, or an iodine atom, with a hydrocarbon solvent having a higher boiling point than the ether solvent, so that the fluoroaryl magnesium derivative and the boron halide react with each other while the ether solvent is distilled out, the solution prepared by dissolving the fluoroaryl magnesium derivative in the ether solvent and the solution prepared by dissolving the boron halide in the ether solvent being added to the hydrocarbon solvent concurrently.

12. The process for preparing a (fluoroaryl)borane compound of claim 11, wherein a temperature at which the fluoroaryl magnesium derivative and the boron halide react with each other while the ether solvent is being distilled out is in a range between 30° C. and 200° C.

13. The process for preparing a (fluoroaryl)borane compound of claim 11, wherein the ether solvant is a cyclic ether.

14. The process for preparing a (fluoroaryl)borane compound of claim 11, wherein an amount of the ether solvent is adjusted in such a manner that a concentration of the fluoroaryl magnesium derivative or the boron halide in the ether solvent is in a range between 0.1 and 80 percent by weight.

15. The process for preparing a (fluoroaryl)borane compound of claim 11, wherein the boiling point of the hydrocarbon solvent is 60° C. or above.

16. The process for preparing of a (fluoroaryl)borane compound of claim 11, wherein an amount of the hydrocarbon solvent is adjusted in such a manner that a concentration of the (fluoroaryl)borane compound is in a range between 0.1 and 50 percent by weight when the fluoroaryl magnesium derivative and the boron halide react with each other while the ether solvent is being distilled out.

17. The process for preparing a (fluoroaryl)borane compound of claim 11, wherein a mole ratio of the fluoroaryl magnesium derivative and the boron halide is in a range between 1.0 and 5.0.

18. The process for preparing a (fluoroaryl)borane compound of claim 11, wherein the fluoroaryl magnesium derivative is pentafluorophenyl magnesium bromide.

19. The process for preparing a (fluoroaryl)borane compound of claim 11, wherein the boron halide is boron trifluoride.

20. The process for preparing a (fluoroaryl)borane compound of claim 11, wherein the boron halide is an ether complex.

21. The process for preparing a (fluoroaryl)borane compound of claim 11, wherein the ether solvent contains diethyl ether and/or tetrahydrofuran.

22. A process for preparing a (fluoroaryl)borane compound expressed by Formula (6):

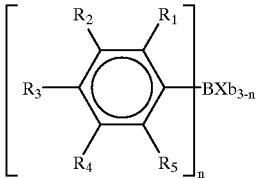

(6)

where each of $R_1$, $R_2$, $R_3$, $R_4$, and $R_5$ represents a hydrogen atom, a fluorine atom, a hydrocarbon group, or an alkoxy group, while at least one of $R_1$–$R_5$ represents a fluorine atom, Xb represents a fluorine atom, a chlorine atom, a bromine atom, or an iodine atom, and n represents 2 or 3, said process comprising mixing a solution prepared by dissolving a fluoroaryl magnesium derivative expressed by Formula (4) below in an ether solvent:

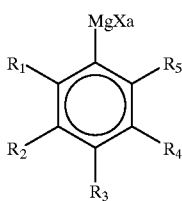

(4)

where each of $R_1$, $R_2$, $R_3$, $R_4$, and $R_5$ represents a hydrogen atom, a fluorine atom, a hydrocarbon group, or an alkoxy group, while at least one of $R_1$–$R_5$ represents a fluorine atom, and Xa represents a chlorine atom, a bromine atom, or an iodine atom, and a solution prepared by dissolving boron halide expressed by Formula (5) below in the ether solvent:

$$BXb_3 \qquad (5)$$

where Xb represents a fluorine atom, a chlorine atom, a bromine atom, or an iodine atom at 80° C. or below, and subsequently mixing a resulting mixed solution with a hydrocarbon solvent having a higher boiling point than the ether solvent, so that the fluoroaryl magnesium derivative and the boron halide react with each other while the ether solvent is being distilled out, the solution prepared by dissolving the fluoroaryl magnesium derivative in the ether solvent and the solution prepared by dissolving the boron halide in the ether solvent being mixed with each other in a temperature range between −40° C. and 70° C.

23. The process for preparing a (fluoroaryl)borane compound of claim 22, wherein the ether solvent is cyclic ether.

24. The Process for preparing a (fluoroaryl)borane compound of claim 22, wherein an amount of the ether solvent is adjusted in such a manner that a concentration of the fluoroaryl magnesium derivative or the boron halide in the ether solvent is in a range between 0.1 and 80 percent by weight.

25. The process for preparing of a (fluoroaryl)borane compound of claim 22, wherein the boiling point of the hydrocarbon solvent is 60° C. or above.

26. The process for preparing a (fluoroaryl)borane compound of claim 22, wherein an amount of the hydrocarbon solvent is adjusted in such a manner that a concentration of the (fluoroaryl)borane compound in a final solution is in a range between 0.1 and 50 percent by weight when the fluoroaryl magnesium derivative and the boron halide react with each other while the ether solvent is being distilled out.

27. The process for preparing a (fluoroaryl)borane compound of claim 22, wherein a mole ratio of the fluoroaryl magnesium derivative and the boron halide is in a range between 1.0 and 5.0.

28. The process for preparing a (fluoroaryl)borane compound of claim 22, wherein the fluoroaryl magnesium derivative is pentafluorophenyl magnesium bromide.

29. The process for preparing a (fluoroaryl)borane compound of claim 22, wherein the boron halide is boron trifluoride.

30. The process for preparing a (fluoroaryl)borane compound of claim 22, wherein the boron halide is an ether complex.

31. The process for preparing a (fluoroaryl)borane compound of claim 22, wherein the ether solvent includes diethyl ether and/or tetrahydrofuran.

32. A process for preparing a (fluoroaryl)borane compound expressed by General Formula (10):

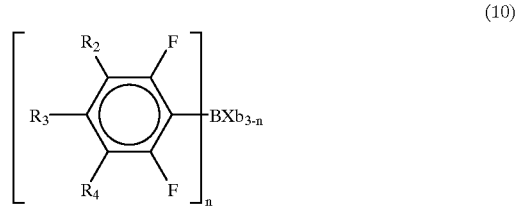

(10)

where each of $R_2$, $R_3$, and $R_4$ represents a hydrogen atom, a fluorine atom, a hydrocarbon group, or an alkoxy group, Xb represents a fluorine atom, a chlorine atom, a bromine atom, or an iodine atom, and n represents 2 or 3, said process comprising mixing a solution prepared by dissolving a fluoroaryl magnesium derivative expressed by Formula (3):

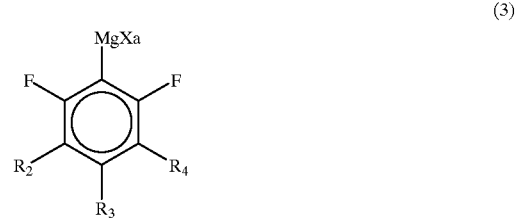

(3)

where each of $R_2$, $R_3$, and $R_4$ represents a hydrogen atom, a fluorine atom, a hydrocarbon group, or an alkoxy group, and Xa represents a chlorine atom, a bromine atom, or an iodine atom by reacting (a) aryl fluoride expressed by Formula (I)

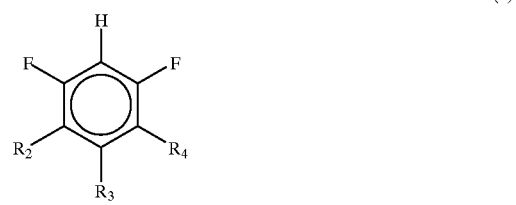

(1)

where each of $R_2$, $R_3$, and $R_4$ represents a hydrogen atom, a fluorine atom, a hydrocarbon group, or an alkoxy group, (b) a hydrocarbon halide expressed by Formula (2):

$$R_0Xa \qquad (2)$$

where $R_0$ represents a hydrocarbon group, and Xa represents chlorine atom, a bromine atom, or an iodine atom, and (c) magnesium with one another in an ether solvent or a mixed solvent of the ether solvent and a hydrocarbon solvent, and subsequently reacting the fluoroaryl magnesium derivative with boron halide expressed by Formula (5)

$$BXb_3 \qquad (5)$$

where Xb is a fluorine atom, a chlorine atom, a bromine atom, or an iodine atom, the fluoroaryl magnesium derivative and the boron halide being reacted with each other by mixing both a solution prepared by dissolving the fluoroaryl magnesium derivative into an ether solvent and a solution prepared by dissolving the boron halide in the ether solvent with a hydrocarbon solvent having a higher of boiling point than the ether solvent while the ether solvent is distilled out.

* * * * *